United States Patent [19]

Swindell et al.

[11] 4,081,673
[45] Mar. 28, 1978

[54] TRANSVERSE TOMOGRAPHY APPARATUS AND METHOD

[75] Inventors: William Swindell; Harrison H. Barrett, both of Tucson, Ariz.

[73] Assignee: University Patents, Inc., Stamford, Conn.

[21] Appl. No.: 675,960

[22] Filed: Apr. 12, 1976

[51] Int. Cl.² .............................................. H01J 39/12
[52] U.S. Cl. ............................ 250/237 R; 250/445 T; 350/162 SF; 250/550
[58] Field of Search ................... 250/475, 550, 445 T, 250/237 G, 237 R; 350/162 SF; 356/71

[56] References Cited

U.S. PATENT DOCUMENTS

| | | | |
|---|---|---|---|
| 2,281,931 | 5/1942 | Frank | 250/44 ST |
| 3,216,318 | 11/1965 | Gaffard | 350/162 SF |
| 3,292,148 | 12/1966 | Giuliano et al. | 350/162 SF |
| 3,540,797 | 11/1970 | Glenn, Jr. | 350/162 SF |
| 3,563,634 | 2/1971 | Parks et al. | 350/162 SF |
| 3,768,907 | 10/1973 | Williams | 350/162 SF |

*Primary Examiner*—Eli Lieberman
*Assistant Examiner*—David K. Moore
*Attorney, Agent, or Firm*—Martin Novack

[57] ABSTRACT

An improved apparatus and method for generating the two-dimensional filtered back-projected image of a slice of an object. In accordance with the invention there is provided a photodetector means and illuminating means directed toward the photodetector means. A carrier means is disposed between the illuminating means and the photodetector means, the carrier means having a plurality of substantially parallel elongated projections on the surface thereof. Each projection has an optical characteristic (transmissivity or reflectivity) representing the density characteristic of the slice of the object as measured at a particular relative rotational angle. A mask means is disposed between the illuminating means and the photodetector, the mask means comprising a plurality of cycles of a substantially sinusoidally shaped pattern of varying amplitude. Means are provided for moving the carrier means and the mask means with respect to each other. Finally, a display or recording means, synchronized with the moving means, is responsive to the output of the photodetector for displaying the back-projected image. In the preferred embodiment of the invention the mask means comprises a movable endless loop and the pattern is a substantially sinusoidal transparency whose amplitude varies between zero and a predetermined maximum. In this embodiment, the mask has an optical characteristic transverse the length thereof which corresponds to a predetermined filter function.

27 Claims, 12 Drawing Figures

PRIOR ART

FIG.1

PRIOR ART

$g_j(X) = f_j(X) \otimes h(X)$

TRANSVERSE TOMOGRAPHY APPARATUS AND METHOD

BACKGROUND OF THE INVENTION

This invention relates to X-ray tomography and, more particularly, to an apparatus and method for imaging cross-sections of objects using transverse tomography techniques.

Using conventional X-ray imaging techniques, a shadow view of a body under examination can be produced, but it does not contain information concerning the depth of details in the body. In many cases it is not possible to distinguish small objects since they are obscured by the structures of larger objects; e.g., bones. This drawback has been overcome to some degree by the development of body-section radiography techniques known as X-ray tomography.

Radiographic transverse tomography attempts to view sections or "slices" which are perpendicular to the axis of a patient. In a "classical" transverse tomographic system, incident X-radiation is passed through an object being studied at an angle and is imaged on a film. In order to image a particular slice, both the film and the object are rotated synchronously during the X-ray exposure. Shadows of points in a single plane of the object are continually projected on to the same place on the film during the rotation, whereas shadows of other parts of the object move in relation to the film. Thus, while the slice of interest is imaged relatively sharply, the resultant picture is overlayed by the motion-blurred images of other parts of the object. As a consequence, the resultant "tomogram" tends to lack contrast and fine detail is obscured.

Recently, digital processing techniques have been applied to the tomographic imaging problem and a degree of success has been achieved whereby blurred images of overlying and underlying planes have been removed so as to permit detection of greater detail. However, digital methods require the processing of extremely large quantities of data, and even fast computers take significantly long times to do the necessary computations. Accordingly, commercial computer tomography equipment is extremely expensive and beyond the financial reach of many who desire it.

In another type of transaxial tomography, a narrow beam of X-rays is employed and only the rays passing through the desired cross-section are incident on a film so, ideally, only information about the particular slice is recorded. The result is a so-called "one-dimensional projection." A plurality of one-dimensional projections can be obtained by passing X-rays through the same cross-section at a number of different rotational angles. The resultant set of one-dimensional projections can be processed optically. Alternatively, the values of each projection can be fed to a computer for digital analysis, whereby the density function of each elemental area in the plane is computed by one of a number of mathematical techniques which utilize iteration, mathematical filtering techniques, and other known solutions.

An early technique for optical processing of a set of one-dimensional projections is disclosed in U.S. Pat. No. 2,281,931 wherein a cylindrical lens system is utilized to optically "enlarge" each one-dimensional projection in a direction perpendicular to the plane of the section. Each enlarged one-dimensional projection is a two-dimensional image and the set of two-dimensional images which result from optically enlarging each one-dimensional projection are superposed with mutual angular displacements that correspond to the rotation angles at which the one-dimensional projections were originally taken. The image ultimately produced in this manner has been referred to as a "layergram" of the cross-section. In recent years, attempts have been made to process the layergram using spatial filtering methods of both optical and digital natures to restore the layergram image which is known to suffer blurring. However, the digital processing techniques again involve the handling and lengthy processing of large amounts of data, which is very expensive. Optical processing techniques toward this same end have generally been found to be either inadequate from a performance standpoint or unduly complex and expensive.

The techniques described in the above-referenced U.S. Pat. No. 2,281,931 is one of a number of image reconstruction techniques which utilize "back projection." Generally, the term "back-projection" implies that the value of a particular point in a projection is assigned to all points on a line perpendicular to the projection. The values of overlapping lines are integrated for all projections. The result is equivalent to back-projecting the values in each one-dimensional projection through the object and integrating their overall effect. As implied above, a simple back-projection yields results which are generally considered inadequate, and it is presently believed that a technique of back-projection, combined with a suitable filtering technique, could yield quality results. However, as emphasized above, such techniques have in the past required expensive and complex systems.

In the copending U.S. patent application Ser. No. 587,352, now U.S. Pat. No. 4,023,036 assigned to the same assignee as the present invention, there is disclosed a novel technique for generating two-dimensional back-projected filtered image of a slice of an object. A carrier means is provided with a plurality of substantially parallel elongated projections on the surface thereof, each projection having an optical characteristic representing the density characteristic of the slice of the object as measured at a particular relative rotational angle. Successive sinusoidal sections of the carrier are imaged and a photodetector is responsive to the imaged sections. The filtered back-projected image is obtained by displaying the output of the photodetector. In one embodiment of the copending application the carrier is in the form of a cylinder which is simultaneously rotated and tilted on its axis to achieve the desired imaging of sinusoidal sections on the carrier. It is an object of the present invention to provide an alternate technique for imaging successive sinusoidal sections such that certain operational advantages are possible.

SUMMARY OF THE INVENTION

The present invention is directed to an improved apparatus and method for generating the two-dimensional back-projected image of a slice of an object. In accordance with the invention there is provided a photodetector means and illuminating means directed toward the photodetector means. A carrier means is disposed between the illuminating means and the photodetector means, the carrier means having a plurality of substantially parallel elongated projections on the surface thereof. (As used herein, the term "disposed between" is intended in the optical sense.) Each projection has an optical characteristic (transmissivity or reflectivity) representing the density characteristic of the slice of the object as measured at a particular relative rotational angle. A mask means is also disposed between the illuminating means and the photodetector, the mask means comprising a plurality of cycles of a substantially sinusoidally shaped pattern of varying amplitude. Means are provided for moving the carrier means and the mask means with respect to each other. Finally, a display or recording means, synchronized with the moving means, is responsive to the output of the photodetector for displaying the back-projected image.

In the preferred embodiment of the invention the mask means comprises a movable endless loop and the pattern is a substantially sinusoidal transparency whose amplitude varies between zero and a predetermined maximum. In this embodiment, the mask has an optical characteristic transverse the length thereof which corresponds to a predetermined filter function so that a filtered back-projection is obtained.

Further features and advantages of the invention will become more readily apparent from the following detailed description when taken in conjunction with the accompanying drawings.

DESCRIPTION OF THE PREFERRED EMBODIMENT

Figure 1:
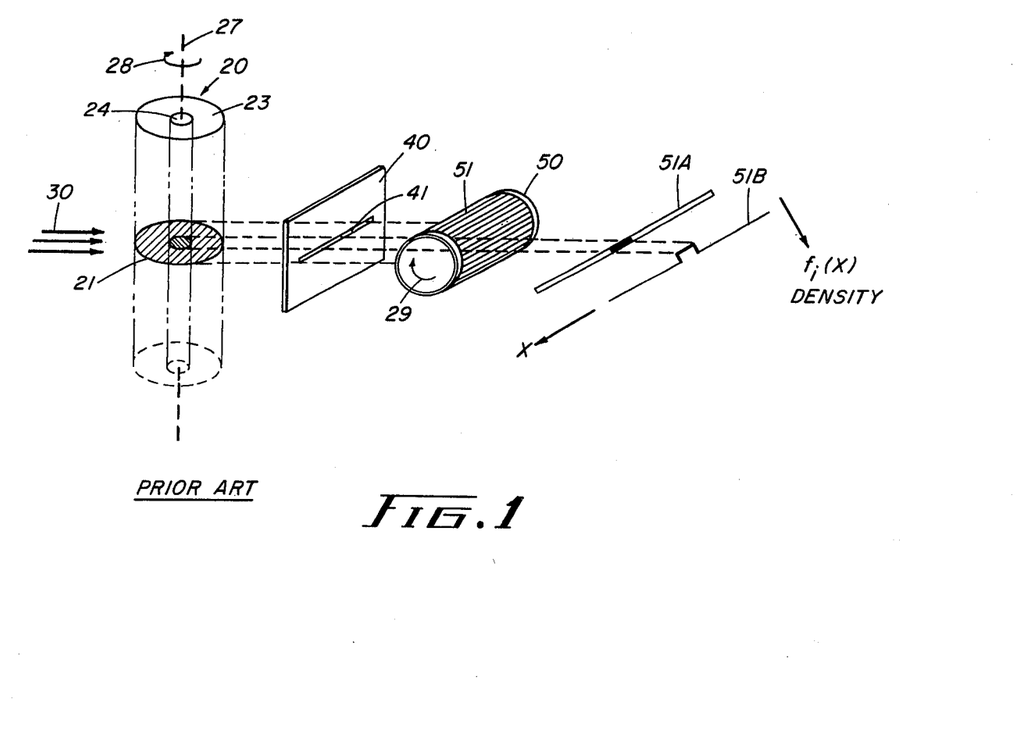
FIG. 1 is a diagramatic representation of a technique for generating one-dimensional projections of a slice of an object.

FIG. 1 illustrates the nature of one-dimensional projections of a body cross-section or slice which can be obtained, for example, in accordance with a technique set forth in the above-referenced U.S. Pat. No. 2,281,931. A body 20, of which a cross-section 21 is to be reproduced, consists of an annular portion 23 of semi-transparent material, such as muscle tissue of a human limb, and a core portion 24 of a material which is less transparent to X-rays, such as bone. A beam of parallel X-rays 30 enamating from a remote source (not shown) passes through body 20, and a narrow portion of the X-ray beam, having a band-shaped cross-section, passes through a narrow elongated slot 41 in a diaphragm 40, which is typically formed of lead. The X-ray beam passing through slot 41 produces a narrow elongated image 51 on X-ray sensitive film member 50, which is provided in the shape of a cylinder. The image 51 can be considered as a one-dimensional projection whose optical characteristic corresponds to the different degrees of absorption of the X-rays by the portions 23 and 24 of the body 20 at section 21.

The elongated strip 51A at the right of FIG. 1 illustrates a simplified version of the one-dimensional projection 51 which is recorded on film 50. It is seen that the central portion of the projection is darkest due to the low transmissivity of core 24 to X-rays and the resultant lesser exposure of the corresponding portion on film 50. (It should be noted that since the thickness of annular portion 23 increases toward the center, the overall transmissivity of this part will also decrease gradually toward the center of body 20 but, for ease of explanation, this gradation is not shown in the simplified illustration of strip 51A or the curve 51B which follows.) The curve 51B illustrates graphically the density function of the slice 21 as a function of length along slot 41, this length being indicated by the coordinate "$x$." The density, indicated as $f_i(x)$, is seen to correspond to the relative transmissivity of the cross-section as a function of $x$; i.e., the inverse of the density chharacteristic.

Returning to the structural portion of FIG. 1, the body 20, and consequently also the section 21 thereof, are rotated about an axis 27 which is normal to the plane of section 21 at the point of rotation, the rotation being represented by curved arrow 28. The cylindrical film 50, which is typically mounted on a drum, is rotated on its axis in angular synchronism with the rotation of body 20. At each of a number of discrete rotational positions, the body and the film 50 are stopped and a one-dimensional projection is recorded (like strip 51A). Accordingly, after a full 360° of rotation the cylindrical film 50 will contain a "set" of one-dimensional projections, i.e., the various $f_i(x)$, each one-dimensional projection having an optical characteristic which represents the density characteristic of the section or slice 21 of the object 20 as measured at a particular relative rotational angle. It will be understood that the one-dimensional projections may be a continuum on the film, but discretely recorded projections will be shown herein for ease of illustration.

Figure 2:
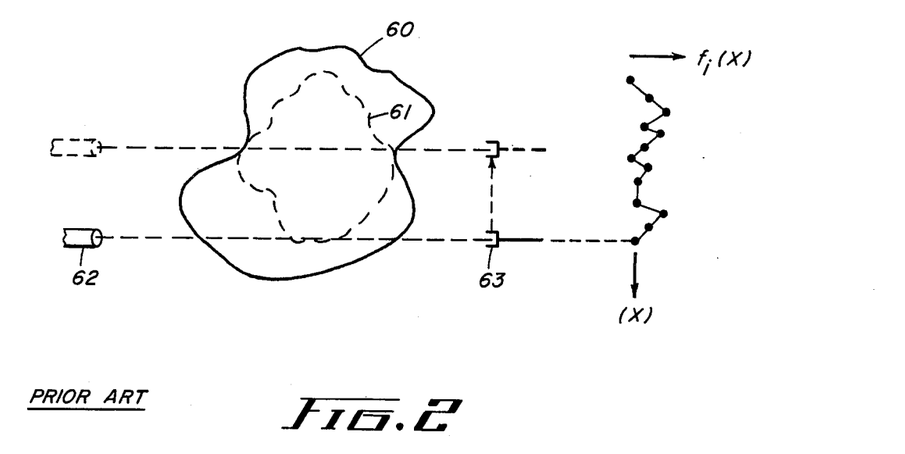
FIG. 2 shows another technique for obtaining one-dimensional projections of a slice of an object.

Referring to FIG. 2, there is shown another known technique of obtaining one-dimensional projections of a slice or section 61 of a three-dimensional body 60. A collimated "pencil" beam of X-rays is generated by a source 62, passed through the section 61, and received by a small-area scintillation detector 63, the output of which is indicated by a point on the graph at the right of FIG. 2. The source 62 and detector 63 are moved synchronously across the slice 61 and an output data value is obtained at each spaced position, each data point representing the intensity of the transmitted X-ray beam. The resultant function $f_i(x)$ is a one-dimensional projection similar in information content to those obtained using the system of FIG. 1, and as designated by the graph 51B of FIG. 1. It will be appreciated that, if desired, one could obtain an optical characteristic such as that of projection 51A from the data of FIG. 2 by utilizing the output of the detector 63 to modulate the intensity of a scanning beam exposing a film strip. More typically, the data points obtained from detector 63 are processed using a digital computer. A "set" of one-dimensional projections, $f_i(x)$, are obtained by taking the depicted measurements at a number of different rotational angles of the section 61, and the totality of the data is processed by a computer to attempt reconstruction of the elemental density function of the two-dimensional slice 61 of object 60. An apparatus for obtaining the desired one-dimensional projections is also set forth in the copending U.S. application Ser. No. 587,329, assigned to the same assignee as the present invention and now abandoned.

Figure 3:
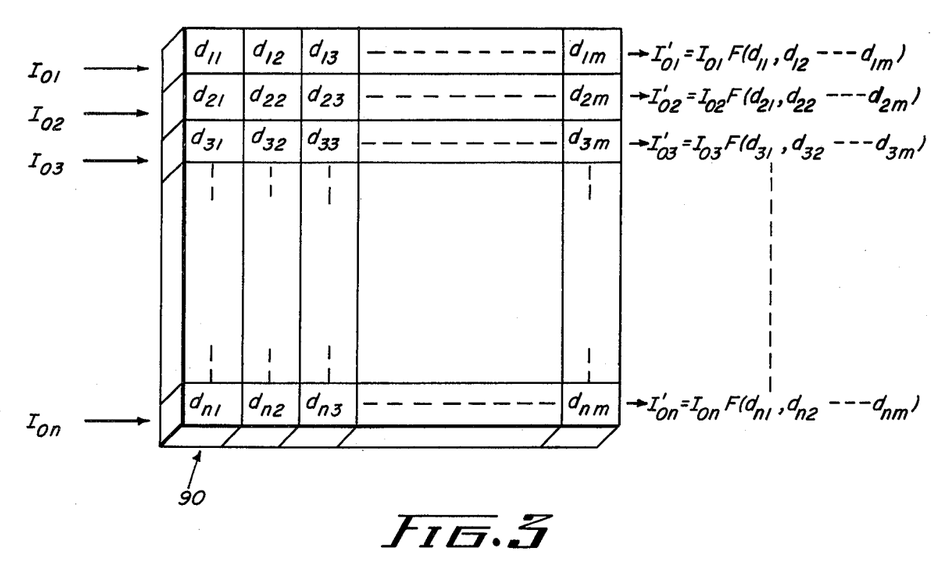
FIG. 3 is a diagram of a slice of an object useful in understanding approaches to obtaining the density characteristic of said slice.
Figure 5:
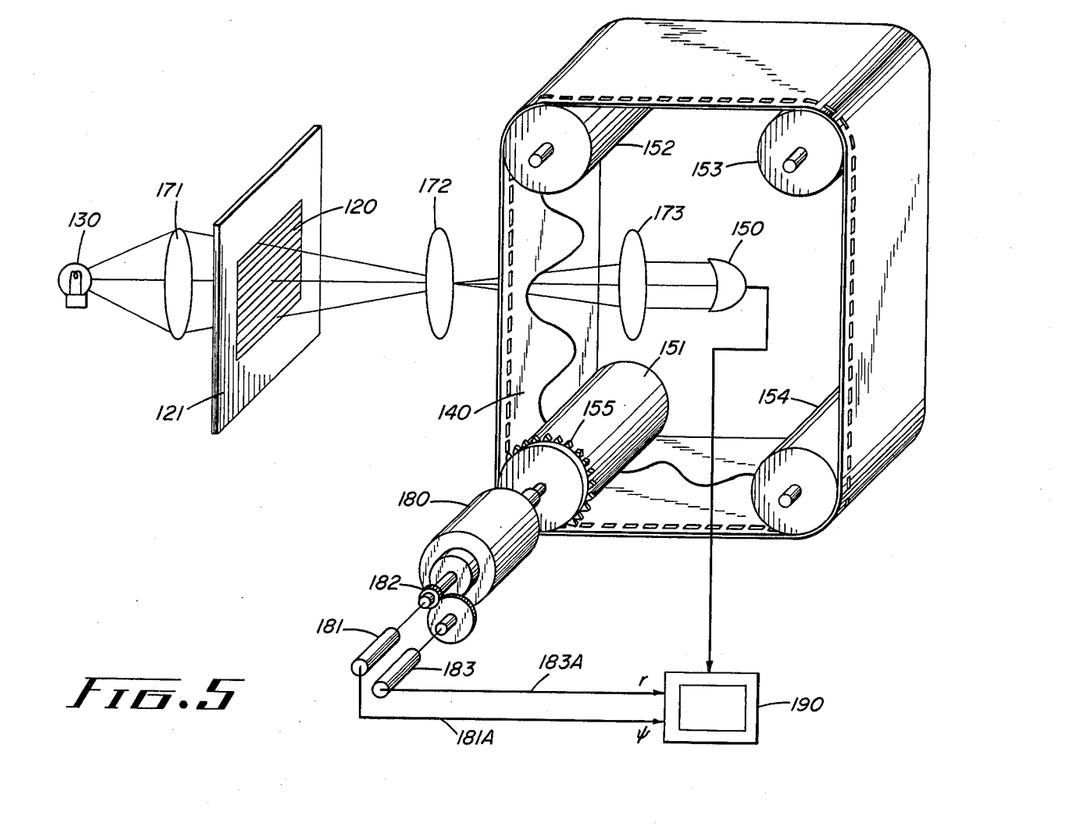
FIG. 5 is an elevational perspective view, partially in schematic block diagram form, of an apparatus in accordance with an embodiment of the invention.

FIG. 3 is helpful in further illustrating the nature of the obtained one-dimensional projections, as well as in understanding approaches to obtaining the density characteristics of a section or slice of an object from such projections, and especially approaches which utilize "back-projection." A thin section or slice 90 under investigation is depicted as being rectangular for ease of explanation. The section is divided into an array of small elemental units which comprise an $m$ by $n$ array wherein each element is designated by its position in the array and assumed to have a density which is to be ultimately determined. Thus, for example, the density of the element in the upper left hand corner is designated by $d_{11}$, its adjacent neighbor to the right has a density designated by $d_{12}$, and so on. The beam, or portion of the beam (e.g., in FIG. 2 or FIG. 1), passing through a particular row of elements is designated by I with two subscripts, the first subscript indicating the reference angle at which the X-ray energy is passed through the slice 90 (a 0° reference angle is shown in FIG. 5, so the first subscript is 0), and the second subscript indicating the relative position of the particular beam or beam portion along the one-dimensional data coordinate (e.g., the $x$ axis in FIGS. 1 and 2). The detected beams, or portions thereof, which have passed through the slice 90 are designated by primed versions of the input beams. Each output is equal to its corresponding input times a function of the elemental densities through which the beam or beam portion has passed. For example, it is seen that $I_{01}'$ is equal to $I_{01}$ times a function of the elemental densities of the first row of the array, as shown. Similarly, the remaining outputs are each also functions of the elemental densities in their corresponding rows. It will be appreciated that in the expressions for the one-dimensional projection values for a particular reference rotational angle (0° for the illustrated case), there are many more unknown than equations. However, it the slice is now rotated on its axis to a number of different positions, and additional one-dimensional projection data values are obtained at each rotational angle, the full "set" of one-dimensional projections will yield a large number of equations which can be used to determine the unknowns; i.e., the individual elemental densities in the slice 90.

As referred to in the Background portion of the specification, the set of one-dimensional projections can be processed by computer using various techniques. One type of prior art solution used an iterative technique wherein assumed elemental density values are assigned to each member of the array. The computer calculates the output intensity values that would be obtained from the model, and these calculated output intensities are compared with the actual output intensities to obtain error values. The error values are examined and used to calculate appropriate modifications of the model which will yield smaller error values, and the process is continued until a model is obtained which yields error values that are considered acceptably small. Depending on the particular algorithm used, it will take at least some minimum number of computations for the model to "converge" to an acceptable state. In any event, the computer must have adequate speed, memory, etc., to obtain a solution within a reasonable time, so the equipment needed can be prohibitively expensive. A number of technique have also been attempted wherein the computer systematically solves the simultaneous equations by classical means or employment of known matrix manipulation methods. Unfortunately, these approaches are also found to require very large numbers of calculations and expensive computer equipment is needed for solution within practical time constraints.

In the "back-projection" image reconstruction technique treated above, the value of a particular data point in a projection is assigned to all points on a line perpendicular to the projection. In terms of FIG. 3, for example, the value $I_{01}'$ would be assigned to each of the elements in the row to which that output intensity is attributed; viz., $d_{11}, d_{12} \ldots d_{1m}$. Similarly the output intensity value $I_{02}'$ is applied to all of the elemental densities in the second row; viz, $d_{21}, d_{22}, \ldots d_{2m}$, and so on for the remaining rows. Next, the output data values of the next one-dimensional projection are assigned in the same manner to each elemental density, and this is done for each relative rotation angle at which a one-dimensional projection was obtained. Thus, at the completion of the back-projection, each elemental density has a final value which equals the sum of all the data values attributable to it during the process previously described. The back-projection process can be performed either on a digital computer or optically, but the results of a simple back-projection have been found inadequate in most cases due to blurring.

Figure 4:
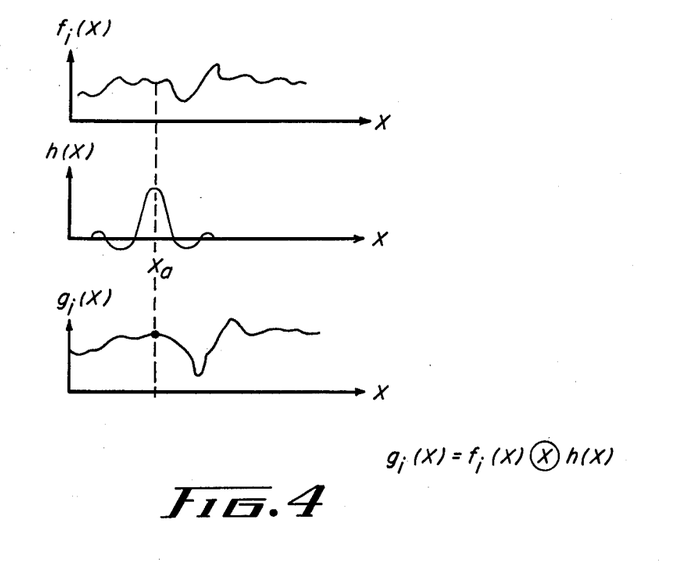
FIG. 4 shows graphs useful in describing the convolution of a filter function with a one-dimensional projection.

In order to derive better results using back-projection techniques, it has been suggested that a technique of "filtering" be used in conjunction with back-projection. The filtering can be thought of as a type of selective "weighting" which aids in restoration of a true density characteristic by removing blurring effects. The filtering can either be done on the one-dimensional projections before the back-projection operation, or it can be done on the reconstructed back-projected image. FIG. 4 illustrates the filtering of a particular one-dimensional projection designated $f_i(x)$ using a filter function designated by $h(x)$. Mathematically, the two functions $f_i(x)$ and $h(x)$ are convolved to obtain the resultant filtered one-dimensional projection which is designated $g_i(x)$. The convolution operation can be visualized graphically by considering the filter function $h(x)$ as being moved along the $x$ axis and a multiplication between $f_i(x)$ and $h(x)$ being performed at each point of the excursion of the filter function. For example, in FIG. 4 the filter function is shown at an abscissa position $x_a$ and the resultant data point on the function $g_i(x)$ (as shown by the dot on the third graph) is obtained by multiplying $h(x)$ at this position by the function $f_i(x)$. This operation is performed at each point along the $x$ axis and the function $g_i(x)$ is obtained in this manner. As disclosed in a publication of Cho et al. in IEEE Transactions on Nuclear Science, Vol. NS-21, page 44 (June, 1974), one-dimensional projections are convolved with a processing function, as just described, the operation being performed on a digital computer.

The type of filtering and back-projection techniques just described, as well as those where convolution is performed after back-projection, involve large numbers of computations when performed on a digital computer, so expensive computing capability is required. Optical techniques have been attempted for performing these operations. For example, it is known that lenses perform Fourier transformation when coherent light is used. However, such systems tend to be limited by such factors as necessary photoreductions and film thickness variations.

Referring to FIG. 5, there is shown an embodiment of an apparatus 100 in accordance with the invention. A carrier of film 120 is supported in an opaque frame 121. The film has recorded thereon a plurality of substantially parallel elongated projection images, each projection image having a transmissivity which represents the density characteristic of a cross-section or slice of an object as measured at a particular relative rotational angle. The film 120 may be recorded in the manner described in conjunction with FIG. 1, or by using variations of the technique described in conjunction with FIG. 2 or in the above-referenced copending U.S. application Ser. No. 587,329. Each projection is of the general type described with refereence to the strip 51A in FIG. 1, and, in the present embodiment, the full 360° of arc of the film 120 contains adjacent projections taken at rotational increments of the object slice in question as it is rotated a full 360°.

Spaced from the film 120 is a movable mask 140, to be described, which is in the form of an endless film loop mounted on a sprocketed roller 151 and idler rollers 152 – 154. A lamp 130 illuminates the film 120 and the light passing therethrough and through the mask 140 is incident on a photodetector 150. In the present embodiment lens 172 images the projections on the film 120 onto the mask 140 and lenses 171 and 173 focus the light source at the detector. It will be understood, however, that various alternative optics can be employed.

The sprocketed roller 151 has a sprocket wheel 155 which engages sprocket holes on the edge of the mask film loop 140. A synchronous motor 180 drives the sprocketed roller 151 at a constant speed and a shaft encoder 181 generates an output signal 181A as a function of the roller position. Gearing 182 steps down the rotational rate of the roller 151 at ratio to be described, and the rotation of gearing 182 is sensed by another shaft encoder 183 which generates an output signal 183A. Signals 181A and 183A synchronize the scan pattern of a display 190 (which could alternately be a recorder) which also receives the output of the photodetector 150 to modulate the brightness of the display. The resultant display or recorded image represents the filtered two-dimensional back-projected image of the slice of the object from which the one-dimensional projections on film 120 were originally made.

Figure 6:
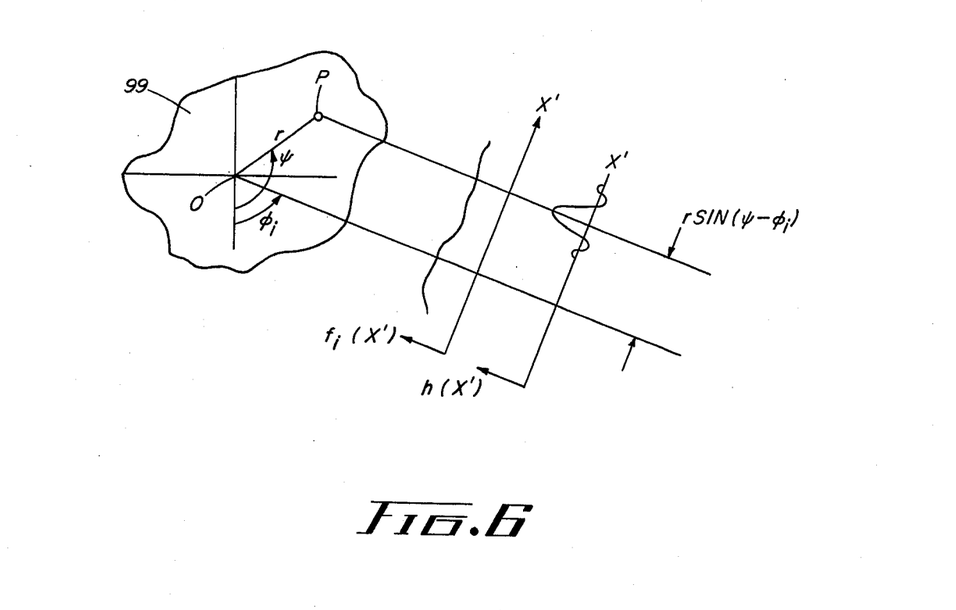
FIG. 6 is a representation of a slice of an object, along with explanatory graphs, which are useful in understanding the invention.
Figure 7:
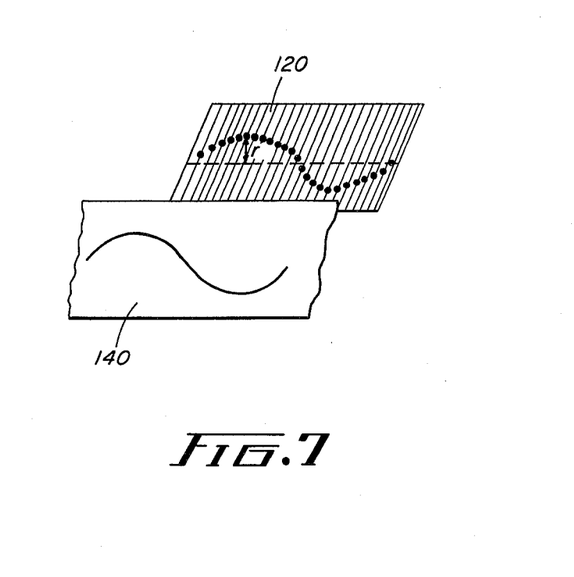
FIG. 7 is a simplified perspective representation of a portion of the invention which is useful in facilitating understanding of the invention.

An understanding of the operation of the apparatus of FIG. 5 is facilitated by examining FIGS. 6 and 7. (Some of the mathematics relating to techniques of transaxial tomography disclosed herein is set forth in the above-referenced publication of Cho et al. which describes the digital convolution of one-dimensional projections with a filter function.) Assume that $f_i(x)$ is the negative logarithm of a one-dimensional projection made at a reference rotational angle $\phi_i$, and assume further that the appropriate filtering function is designated $h(x)$ (see, e.g., FIG. 4). A filtered projection can be represented by the following convolution integral:

$$\int_{-\infty}^{\infty} f_i(x - x')h(x')dx' \quad (1)$$

The desired complete filtered image can be obtained, as previously discussed, by back-projecting each of the filtered projections into the object space and summing over all $\phi_i$. Mathematically, this operation is described by the sum $$\Sigma \left[ \int_{-\infty}^{\infty} f_i(x - x')h(x')dx' \right]_{x=r\sin(\psi-\phi_i)} \quad (2)$$

where $(r,\psi)$ are the polar coordinates of a point in the object that is being reconstructed.

In the present invention the mathematical operation of summation (2) is performed using a moving mask having a plurality of cycles of a substantially sinusoidally shaped pattern of varying amplitude, the itegration being performed by the photodetector 150. Specifically, the mask 140 has N cycles of sinusoidally shaped transparency thereon which vary continually in amplitude from zero to a predetermined maximum. In the present embodiment, each full cycle of sinusoid is dimensioned to image the set of projections of film 120. However, as will become understood, the invention could be practiced in alternate ways, such as by having an integral number of half cycles of sinusoid image an appropriate set of projections taken over a range of rotational angles which correspond to the number of half cycles of sinusoid utilized.

The geometrical rationale can be better understood with reference to FIG. 7 which illustrates a portion of the mask 140 and one cycle of sinuosidal transparency thereof imaging the set of projections on the film 120. If the instantaneous amplitude of the sinusoid is designated $r$, it can be shown that a "point absorber" at a point $(r,\psi)$ in the original object (from which the projections 120 were made) would yield the illustrated sinusoidal pattern on the projections as the object is rotated through 360° of angles $\phi_1$ (see FIG. 6). Accordingly, the summation representative of each back-projected point of expression (2) is represented by the instantaneous output of photodetector 150. The relatively slow amplitude variation of the sinusoid is equivalent to varying the radius of the reconstructed point and the relatively fast phase variation of the sinusoid (imaged on the projections) is equivalent to varying the angle $\psi$ of the reconstructed point. These variations yield a spiral reconstruction pattern which is obtained on a display or recorder 190 by varying the radius of the scan in accordance with the signal 183A from shaft encoder 183 and varying the angular position of the scan in accordance with the signal 181A from shaft encoder 181. (If the display has conventional horizontal and vertical deflection means, the appropriate deflection signals are readily obtained from $r\sin\psi$ and $r\cos\psi$ respectively.) The circumference of the sprocketed roller 151 is set equal to the period of one cycle of the sinusoidal pattern on mask 140, so the output of the shaft encoder 181 varies directly with $\psi$, as desired. Gearing 82 steps down the rotational rate of the roller 151 by a factor of N. Since there are N cycles of sinusoid on the mask, the shaft encoder will cycle once for each complete cycle of the mask, and r will thereby vary directly with the sinusoidal amplitude, as desired.

Figure 8:
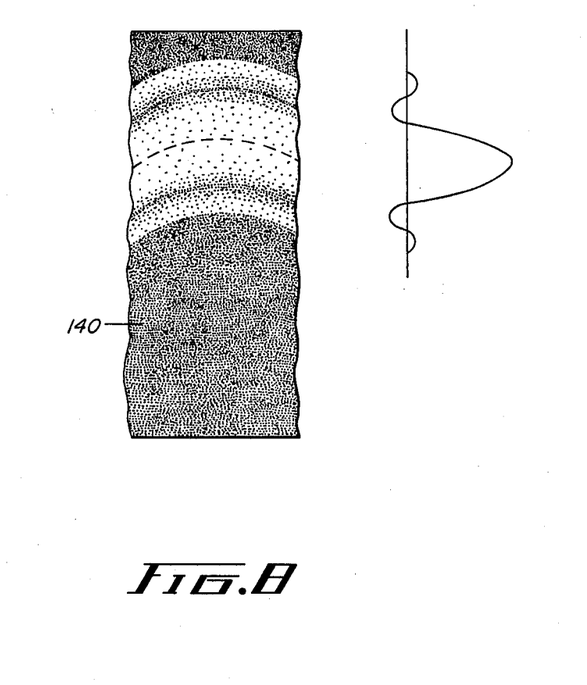
FIG. 8 illustrates a portion of the mask means in accordance with an embodiment of the invention.
Figure 9:
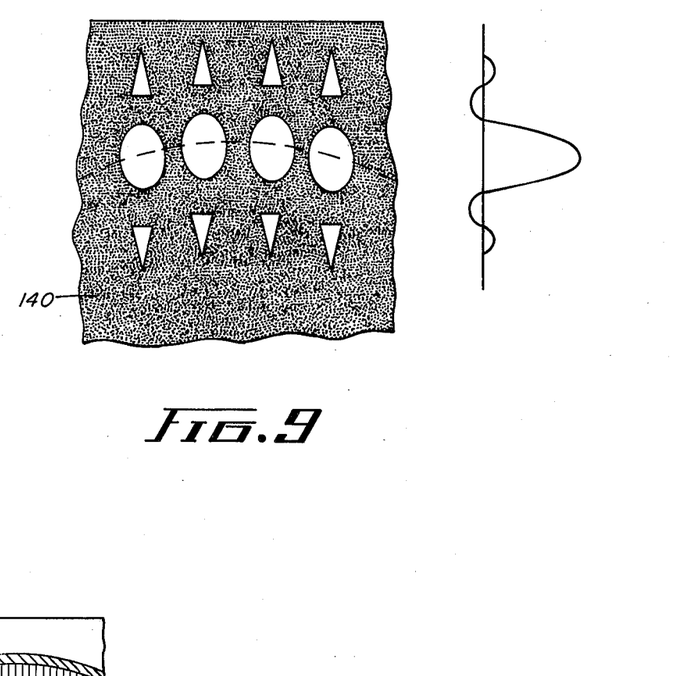
FIG. 9 illustrates a portion of another mask means in accordance with an embodiment of the invention.

For purposes of understanding the manner in which the apparatus of FIG. 5 generates a back-projected image, the diagram of FIG. 7 illustrates a simple sinusoidal slit as the transparency through which the projections are viewed. It is preferred, however, that the mask also provide a filtering function of the type illustrated in conjunction with FIG. 4. A portion of a suitable mask is shown in FIG. 8. Laterally across the mask of FIG. 8 the distribution of film transmittance should vary as the function $h(x)$ shown in FIG. 4 and reproduced in FIG. 8. However, since this function is bipolar, a suitable technique must be used to simulate the negative-going portions thereof. For example, the $h(x)$ curve of FIG. 4 could be translated by a constant amount to a higher (positive) reference level so that its transmittance is always positive. In such case, the output of the photodetector will always be higher than required by the constant amount, so a video bias level can be employed to cancel the resultant undesired "background" brightness level. If desired, a binary distribution of densities (without grey scale) could be utilized, as illustrated in FIG. 9. In such case the shaped apertures on the film have areas which approximate the filter function of FIG. 4.

Figure 10A:
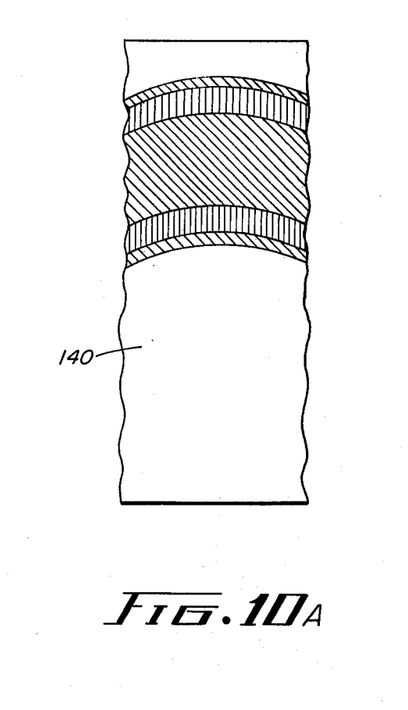
FIG. 10A illustrates a portion of another mask means in accordance with an embodiment of the invention and FIG. 10B shows a modification of FIG. 5 for use in conjunction with the mask of FIG. 10A.
Figure 10B:
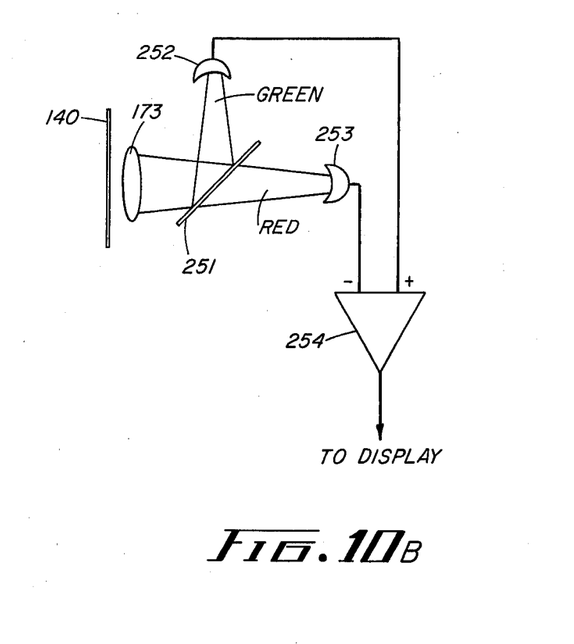

An alternate scheme for dealing with a bipolar filter function is illustrated in FIGS. 10A and 10B wherein the transverse sections corresponding to the positive and negative-going lobes of FIG. 4 are respectively colored, e.g., green and red, respectively, with each having a transmittance which varies laterally across the film in accordance with the filter function of FIG. 4. FIG. 10B shows that portion of the apparatus of FIG. 5 which is utilized in conjunction with the mask illustrated in FIG. A. A dichroic mirror 251 separates the red and green image portions and photodetectors 252 and 253 produce signals proportional to the positive and negative components, respectively, of the filter function. These signals are coupled to a difference amplifier 254 whose output is, in turn, coupled to the display 190 of FIG. 5. It will be appreciated that various alternative techniques can be employed to achieve the bipolar filtering function. For example, the color "coded" portions of FIG. A could be "coded" with orthogonal polarizations and then "read" using a polarizing beam-splitter. Alternatively, spatial coding could be achieved by splitting the incident beam and then employing separate synchronized "positive" and "negative" masks with associated photodetectors whose outputs are subtracted as in FIG. 10B.

Figure 11:
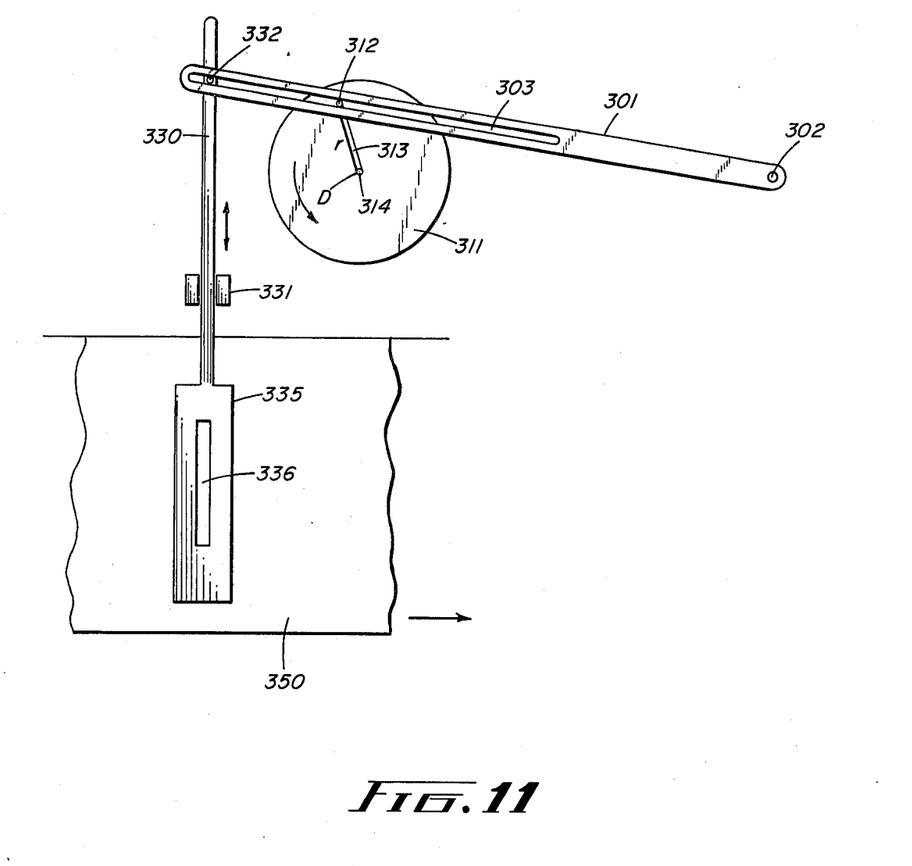
FIG. 11 is a schematic representation illustrating a technique for generating the mask means of FIG. 5.

FIG. 11 shows an optical/mechanical technique for generating the mask 140 of FIG. 5. This technique obtains the desired sinusoidal pattern by simulating the projection of point absorbers in an original object as they are rotated for successive exposures. A slotted rod 301 is pivotally mounted at 302 and is driven in an arc by a peg 312 which fits in the slot 303 of rod 301. The peg is movable (by means not shown) radially in a track 313 of a wheel 311 which is rotated synchronously (by means not shown) about its center 314. A sliding bar 330 is constrained to move in the vertical direction, in this configuration, by guides 331. The bar 330 has a peg 332 thereon which slides in the slot 303 or rod 301. An unexposed photographic film 350 is moved at a substantially constant speed (by means not shown) along the horizontal direction. The film speed is synchronized with the angular rotational rate of the wheel 311. A member 335 having a vertical slit 336 therein is mounted on the end of bar 330. The film 350 is exposed through the slit 336 by a light source (not shown). The slit is covered with a film having a graded transmittance which corresponds to the function $h(x)$ of FIG. 4, or any desired filter function. Alternately, the slit could be clear but shaped to have an effective varying transmittance along its length which corresponds to the desired filter function. In operation, as the peg 312 rotates around center 314 each point on the slit traces out a substantially sinusoidal pattern on the film 350. The amplitude of each period of sinusoid depends on the instantaneous radius $r$ of the peg 312. The radius $r$ is slowly increased at a constant relatively slow rate (or can be incremented after each rotation), and the number of rotations of wheel 311 necessary for a full sweep of the radius is determinative of the number of cycles of sinusoid exposed on the film. The distances between point 302, center 314 and bar 330 may be proportional to the respective distances between the X-ray source, the axis of rotation of the object being examined, and the recording surface, so that each cycle of sinusoid pattern simulates the projection of a point absorber at a particular radius in the original object as it is rotated for successive exposures.

As noted above, the slit 336 could alternately be a shaped aperture and, also, a flashing light source could be provided for discrete exposures. Appropriately coloring or polarizing regions could also be employed to obtain mask patterns such as in FIG. 10A. Also, a binary mask could be employed at the slit 336. If desired, "positive" film 350 may be used to make the mask 140 (FIG. 5) directly. For a binary mask 140, it will be understood that substitutes for photographic film can be used; e.g., a metal film etched using the exposed film 350 as a pattern, or any suitable material preferably having strength and stability.

The invention has been described with reference to particular embodiments, but variations within the spirit and scope of the invention will occur to those skilled in the art. For example, it will be understood that while the preferred embodiment illustrates the mask as being a movable endless loop, a mask which reciprocates back and forth could also be used. Also, the mask could, if desired, be held stationary while the projections are moved, either directly or optically, with respect to the mask. Further, it will be understood that while a mechanical technique for generating the mask is shown, the mask could alternatively be generated by electronic control of an optical display, such as a computer driven cathode ray tube. Finally, while a mask having a pattern in the form of a transparency is preferred, it will be understood that a reflective mask could be employed.

We claim:

1. Apparatus for generating a two-dimensional back-projected image of a slice of an object, comprising:
    photodetector means;
    illuminating means directed toward said photodetector means;
    carrier means disposed between said illuminating means and said photodetector means, said carrier means having a plurality of substantially parallel elongated projections on the surface thereof, each projection having an optical characteristic representing the density characteristic of said slice of the object as measured at a particular relative rotational angle;
    mask means also disposed between said illuminating means and said photodetector means, said mask means comprising a plurality of cycles of a substantially sinusoidally shaped pattern of varying amplitude;

means for moving said carrier means and said mask means with respect to each other; and display means responsive to the output of said photodetector means for displaying the back-projected image.

2. Apparatus as defined by claim 1 wherein said substantially sinusoidally shaped pattern is a transparency.

3. Apparatus as defined by claim 2 wherein said mask means comprises a movable endless loop.

4. Apparatus as defined by claim 2 wherein said plurality of cycles comprises an integral number of half cycles.

5. Apparatus as defined by claim 4 wherein the amplitude of said substantially sinusoidal transparency varies between zero and a predetermined maximum.

6. Apparatus as defined by claim 2 wherein said optical characteristic is transmissivity.

7. Apparatus as defined by claim 3 wherein said optical characteristic is transmissivity.

8. Apparatus as defined by claim 2 wherein said mask has an optical characteristic transverse the length thereof which corresponds to a predetermined filter function.

9. Apparatus as defined by claim 3 wherein said mask has an optical characteristic transverse the length thereof which corresponds to a predetermined filter function.

10. Apparatus as defined by claim 2 wherein said display is synchronized with said moving means.

11. Apparatus as defined by claim 9 wherein said display is synchronized with said moving means.

12. A method for generating a two-dimensional back-projected image of a slice of an object, comprising the steps of:

providing a plurality of substantially parallel elongated projections on a carrier, each projection having an optical characteristic representing the density characteristic of said slice of the object as measured at a particular rotational angle;

illuminating the carrier;

disposing a mask to receive illumination from said carrier, said mask comprising a plurality of cycles of substantially sinusoidal transparency of varying amplitude;

moving said carrier and said mask with respect to each other;

detecting the intensity of the illumination passing through said mask; and displaying the back-projected image of the slice as a function of the detected intensity.

13. The method as defined by claim 12 wherein the step of moving the carrier and mask with respect to each other comprises moving an endless loop mask with respect to a stationary carrier.

14. The method as defined by claim 13 wherein said step of displaying is synchronized with the moving of said mask.

15. Apparatus for generating a two-dimensional back-projected image of a slice of an object from a carrier having a plurality of substantially parallel elongated projections on the surface thereof, each projection having an optical characteristic representing the density characteristic of said slice of the object as measured at a particular relative rotational angle, comprising:

photodetector means;

illuminating means directed toward said photodetector means;

means for disposing said carrier means between said illuminating means and said photodetector means;

mask means also disposed between said illuminating means and said photodetector means, said mask means comprising a plurality of cycles of a substantially sinusoidally shaped pattern of varying amplitude;

means for moving said carrier means and said mask means with respect to each other; and display means responsive to the output of said photodetector means for displaying the back-projected image.

16. Apparatus as defined by claim 15 wherein said substantially sinusoidally shaped pattern is a transparency.

17. Apparatus as defined by claim 15 wherein said mask means comprises a movable endless loop.

18. Apparatus as defined by claim 16 wherein said mask means comprises a movable endless loop.

19. Apparatus as defined by claim 16 wherein said plurality of cycles comprises an integral number of half cycles.

20. Apparatus as defined by claim 19 wherein the amplitude of said substantially sinusoidal transparency varies between zero and a predetermined minimum.

21. Apparatus as defined by claim 16 wherein said optical characteristic is transmissivity.

22. Apparatus as defined by claim 18 wherein said optical characteristic is transmissivity.

23. Apparatus as defined by claim 16 wherein said mask has an optical characteristic transverse the length thereof which corresponds to a predetermined filter function.

24. Apparatus as defined by claim 17 wherein said mask has an optical characteristic transverse the length thereof which corresponds to a predetermined filter function.

25. Apparatus as defined by claim 16 wherein said display is synchronized with said moving means.

26. Apparatus as defined by claim 24 wherein said display is synchronized with said moving means.

27. Apparatus as defined by claim 16 wherein said means for disposing said carrier means comprises an opaque frame.

* * * * *